United States Patent [19]
Lawyer et al.

[11] Patent Number: 6,042,848
[45] Date of Patent: Mar. 28, 2000

[54] ENHANCEMENT OF ANTIMICROBIAL PEPTIDE ACTIVITY BY METAL IONS

[75] Inventors: Carl H. Lawyer; Kounosuke Watabe, both of Springfield, Ill.

[73] Assignee: The Board of Trustees of Southern Illinois University, Springfield, Ill.

[21] Appl. No.: 08/911,794

[22] Filed: Aug. 15, 1997

Related U.S. Application Data

[60] Provisional application No. 60/023,983, Aug. 15, 1996.

[51] Int. Cl.[7] .......................... A61K 33/22; A61K 33/34; A61K 33/38; A61K 38/02
[52] U.S. Cl. .......................... 424/604; 424/618; 424/630; 424/632; 424/633; 424/634; 424/635; 424/637; 424/638; 424/639; 424/649; 424/657; 424/682; 514/2; 514/12; 514/21
[58] Field of Search .................................. 422/28, 32, 37; 514/2, 12, 21; 424/607, 608, 618, 619, 622, 630, 631, 632, 633, 634, 635, 636, 637, 638, 639, 640, 649, 657, 658, 659, 660, 677, 679, 682

[56] References Cited

U.S. PATENT DOCUMENTS

| | | | |
|---|---|---|---|
| 4,670,178 | 6/1987 | Huth et al. | 252/95 |
| 4,720,483 | 1/1988 | Jansz et al. | 514/11 |
| 5,221,664 | 6/1993 | Berkowitz et al. | 514/6 |
| 5,242,902 | 9/1993 | Murphy et al. | 514/12 |
| 5,547,939 | 8/1996 | Selsted | 514/14 |
| 5,610,139 | 3/1997 | Ohta et al. | 514/13 |
| 5,681,591 | 10/1997 | Park et al. | 424/616 |
| 5,691,304 | 11/1997 | Kapa et al. | 514/8 |
| 5,773,694 | 6/1998 | Broeckaert et al. | 800/205 |
| 5,804,558 | 9/1998 | Lehrer et al. | 514/13 |

FOREIGN PATENT DOCUMENTS

| | | |
|---|---|---|
| 0728478A1 | 8/1996 | European Pat. Off. . |
| WO93/01723 | 2/1993 | WIPO . |
| WO95/13057 | 5/1995 | WIPO . |
| WO95/27497 | 10/1995 | WIPO . |

OTHER PUBLICATIONS

Wyngaarden et al. Cecil Textbook of Medicine, 19th ed. Phila.: W.B. Saunders Co. pp. 1303–1306, 1992.

Hodson et al, Aerosol Carbenicillin and Gentamicin . . . The Lancet. pp. 1137–1139, Nov. 21 1981.

Jeffrey J. Smith, et al.; Cystic Fibrosis Airway Epithelia Fail to Kill Bacteria Because of Abnormal Airway Surface Fluid (Apr. 19, 1996) *Cell,* vol. 85; pp. 229–236.

Scott D. Mills, et al., A Two–Component Regulatory System Required for Copper–Inducible Expression of the Copper Resistance Operon of *Pseudomonas syringae* (Mar., 1993) *Journal of Bacteriology,* vol. 175(6); pp. 1656–1664.

Michael Zasloff; Magainins, a class of antimicrobial peptides from Xenopus skin: Isolation, characterization of two active forms, and partial cDNA sequence of a precursor (Aug., 1987) *Proc. Natl. Acad. Sci. USA;* vol. 84; pp. 5449–5453.

*Primary Examiner*—Jeffrey E. Russel
*Attorney, Agent, or Firm*—Senniger, Powers, Leavitt & Roedel

[57] ABSTRACT

Provided are methods for maintaining or enhancing the antimicrobial activity of antimicrobial peptides, lytic peptides, and peptide-derived antibiotics by the use of metal ions. Also provided are pharmaceutical and other compositions comprising such peptides and/or at least one metal ion. Also provided are therapeutic and other methods for controlling the growth of undesirable or pathogenic microorganisms in various loci or milieu in, on, or outside the body employing these peptides and metal ions. Also provided are kits comprising containers containing a peptide and a metal ion(s), respectively.

27 Claims, 2 Drawing Sheets ature of the invention

SEQUENCE LISTING

<160> NUMBER OF SEQ ID NOS: 3

<210> SEQ ID NO 1
<211> LENGTH: 11
<212> TYPE: PRT
<213> ORGANISM: Salmonella sp.

<400> SEQUENCE: 1

Glu Val Arg Glu Asp Asp Asp Asp Ala Glu Met
1               5                   10

<210> SEQ ID NO 2
<211> LENGTH: 11
<212> TYPE: PRT
<213> ORGANISM: Pseudomonas syringae

<400> SEQUENCE: 2

Gly Val Trp Glu Trp Glu Lys Glu Gly Arg Met
1               5                   10

<210> SEQ ID NO 3
<211> LENGTH: 13
<212> TYPE: PRT
<213> ORGANISM: Sus scrofa

<400> SEQUENCE: 3

Val Arg Arg Phe Pro Trp Trp Trp Pro Phe Leu Arg Arg
1               5                   10

ENHANCEMENT OF ANTIMICROBIAL PEPTIDE ACTIVITY BY METAL IONS This application claims the benefit of priority of U.S. Provisional Application Ser. No. 60/023,983, filed Aug. 15, 1996.

BACKGROUND OF THE INVENTION

1. Field of the Invention

The present invention relates to the use of antimicrobial peptides, lytic peptides, and peptide-derived antibiotics. More specifically, the present invention relates to enhancement of the antimicrobial activity of these peptides by the use of metal ions. Metal ions exert this enhancing effect when administered or employed prior to, simultaneously with, or after application or administration of these peptides. The present invention provides broad spectrum antimicrobial compositions which are useful in preventative and therapeutic applications, treatment of infections, treatment and disinfection of various types of surfaces, etc.

2. Description of Related Art

Cationic antimicrobial peptides kill bacteria. However, their antibacterial effects are inhibited by various factors, including cations such as $Na^{++}$, $Ca^{++}$, and $Mg^{++}$, present at physiological ionic strength in normal plasma and other body fluids (Zasloff (1987) Proc. Natl. Acad. Sci. USA 84:5449–5453). This limits their usefulness as therapeutic drugs, and has interfered with, or prevented, the development of therapeutically useful cationic antimicrobial peptide compositions.

The discovery of means for overcoming the foregoing problems and augmenting the antibiotic activity of antimicrobial peptides would therefore aid in the development of these peptides as useful drugs, disinfecting agents, etc. In particular, agents that could be easily applied or administered along with these peptides to alter the ionic milieu would facilitate bacterial killing in vitro or in vivo.

SUMMARY OF THE INVENTION

In response to the need for a method of preserving or enhancing the antimicrobial effectiveness of antimicrobial peptides, etc., the present inventors have surprisingly discovered that a variety of metal ions can be used to maintain or enhance the biological activity of these peptides. This effect is ion concentration-dependent, and can be used to advantage in preparing effective pharmaceutical and other compositions, and in therapeutic methods, where it is necessary or desirable to maintain or enhance the antimicrobial activity of various antimicrobial peptides.

The compositions and methods disclosed herein provide improved antibiotic efficacy of antimicrobial peptides, improved antibiotic potency of antimicrobial peptides, lower toxicity, reduced side effects, and reverse the marked inhibition of the antimicrobial effects of antimicrobial peptides, lytic peptides, and peptide-derived antibiotics caused by ions such as $Na^{++}$, $Ca^{++}$, $Mg^{++}$, etc., that has prevented or interfered with the development of therapeutically useful cationic antimicrobial peptides. These compositions and methods are useful in the control of, for example, gram positive bacteria, gram negative bacteria, and fungi, including, but not limited to, Pseudomonas aeruginosa, staphylococcus, E. coli, Salmonella, Aspergillus, and Candida albicans.

Further scope of the applicability of the present invention will become apparent from the detailed description and drawings provided below. However, it should be understood that the following detailed description and examples, while indicating preferred embodiments of the invention, are given by way of illustration only since various changes and modifications within the spirit and scope of the invention will become apparent to those skilled in the art from this detailed description.

BRIEF DESCRIPTION OF THE DRAWINGS

The above and other objects, features, and advantages of the present invention will be better understood from the following detailed description taken in conjunction with the accompanying drawings, all of which are given by way of illustration only, and are not limitative of the present invention, in which.

DETAILED DESCRIPTION OF THE INVENTION

The following detailed description is provided to aid those skilled in the art in practicing the present invention. Even so, this detailed description should not be construed to unduly limit the present invention as modifications and variations in the the embodiments discussed herein can be made by those of ordinary skill in the art without departing from the spirit or scope of the present inventive discovery.

The contents of each of the references cited herein are herein incorporated by reference in their entirety.

The effectiveness of copper ions in the range 0.01 mM to 10 mM in enhancing the antimicrobial activity of various peptides is described below.

EXAMPLE 1

Enhancement of Tracheal Antimicrobial Peptide Activity by Copper Ions

Cystic fibrosis airway fluid fails to kill bacteria, perhaps due to the involvement of a defensin (Smith (1996) Cell 85:229). While the Cu concentration in normal serum is in the range from approximately 0.01 to 0.024 mM, the concentrations in normal and cystic fibrosis airway fluid have not been determined. PhoQ gene mutations produce defensin resistance in Salmonella, and dysregulate the response of the bacteria to altered magnesium concentrations. The putative magnesium binding anionic region is EVREDDDDAEM SEQ ID NO:1). Copper ion regulation is similarly sensed and controlled by the putative Cu binding anionic site GVWEWEKEGRM (SEQ ID NO:2) in the corresponding periplasmic region in copper resistance sensor proteins COPS of Pseudomonas syringae (Mills (1993) J. Bacteriol. 175:1656) and pcos in E. coli. We therefore tested the effect of varying copper ion concentrations on the activity of the airway beta-defensin Tracheal Antimicrobial Peptide (TAP). The ability of copper ions to increase the killing of bacteria by TAP in a concentration-dependent manner is shown by the following experiment.

Bovine TAP was synthesized and purified to a single HPLC peak. Bactericidal assay was carried out by growing wild-type E. coli in tryptic soy broth (TSB) until the $OD_{600}$ reached 0.2. Cells were then diluted in 50 µl 10 mM NaPO$_4$ buffer, pH 7.4, to 4×10$^5$ cells/ml. Ten µg/ml TAP and 0.01 to 10 mM CuSO$_4$ were added, and the mixtures were incubated for 30 minutes at 37° C. Five Al samples were plated on L-agar, and the plates were incubated at 37° C. overnight. Colonies were then counted.

Figure 1:
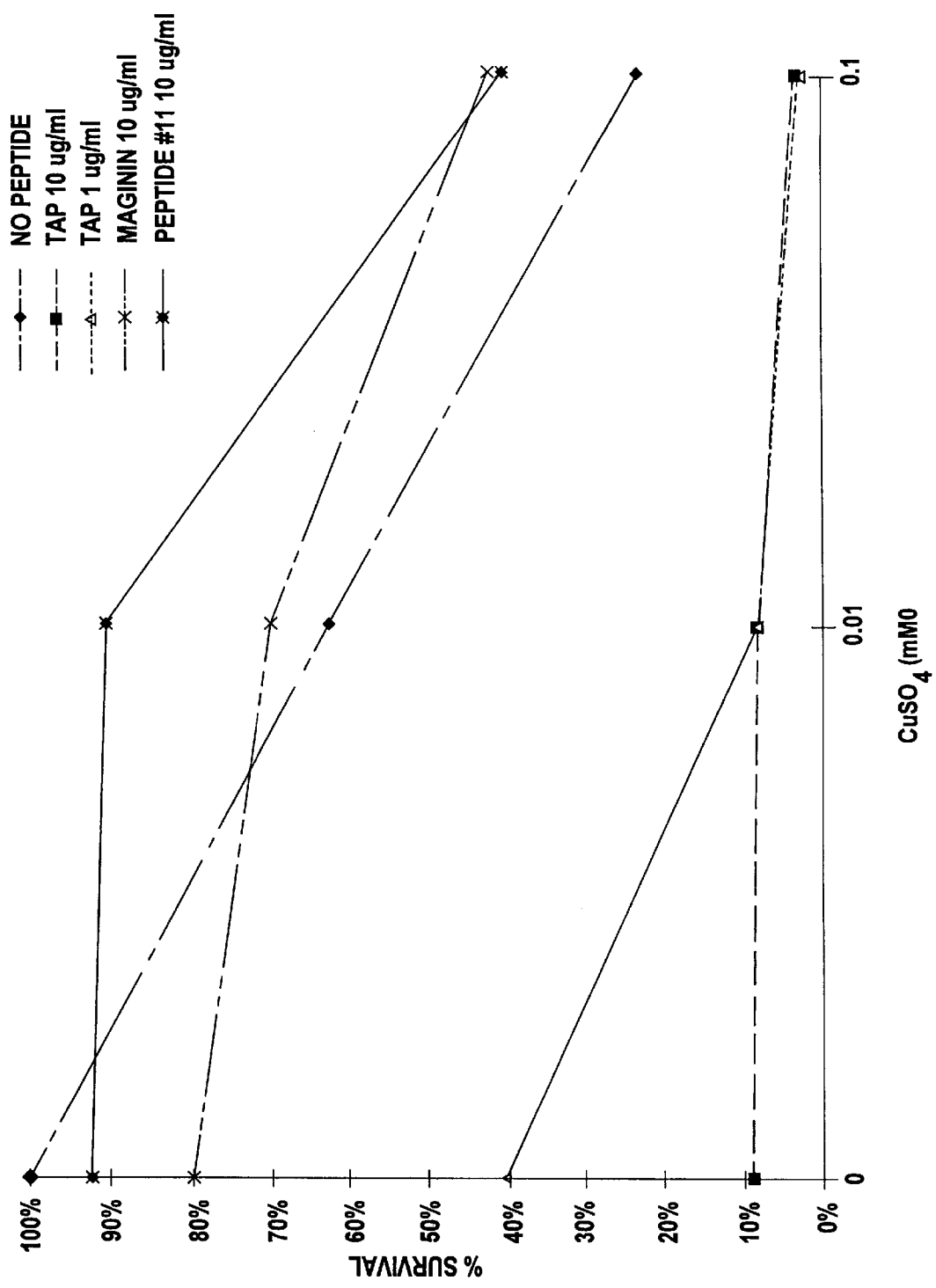
FIG. 1 shows the effects of 0.01 to 0.1 mM $CuSO_4$ on the survival of E. coli in the presence of Tracheal Antimicrobial Peptide (TAP; 1 μg/ml and 10 μg/ml); magainin (10 μg/ml); and peptide #11 (10 μg/ml).

The results are shown in Table 1 and FIG. 1, where it can be seen that CuS0$_4$ in the range from 0.01 to 0.1 mM the antimicrobial activity of TAP at both 1 µg/ml /ml.

TABLE 1

Effect Of Cu$^{++}$ On The Survival of *E. coli*
In the Presence of Various Antimicrobial Peptides

| No Peptides | # COLONIES | CuSO$_4$(m | % SURVIVAL No Peptide | TAP 10 ug | TAP 1 ug/ | Magainin | Peptide #11 |
|---|---|---|---|---|---|---|---|
| 0 | 2858 | 0 | 100% | 9% | 40% | 80% | 92% |
| 0 | 1776 | 0.01 | 62% | 8% | 8% | 70% | 90% |
| 0 | 640 | 0.1 | 22% | 2% | 2% | 41% | 39% |
| 0 | 443 | 1 | 16% | | | | |
| 0 | 211 | 10 | 7% | | | | |

| TAP (ug/ml) | #COLONIES | CU(mM) | % SURVIVAL |
|---|---|---|---|
| 0 | 1335 | 0 | 100% |
| 10 | 119 | 0 | 9% |
| 10 | 106 | 0.01 | 8% |
| 10 | 32 | 0.1 | 2% |

| Magainin (ug/ml) | #COLONIES | Cu(mM) | % SURVIVAL |
|---|---|---|---|
| 0 | 2374 | 0 | 100% |
| 10 | 1895 | 0 | 80% |
| 10 | 1654 | 0.01 | 70% |
| 10 | 975 | 0.1 | 41% |

| Peptide #11 (ub/ml) | #COLONIES | Cu(mM) | % SURVIVAL |
|---|---|---|---|
| 0 | 2500 | 0 | 100% |
| 10 | 2310 | 0 | 92% |
| 10 | 2255 | 0.01 | 90% |
| 10 | 984 | 0.1 | 39% |

These results demonstrate that CuSO$_4$ enhances bacterial killing in a concentration-dependent manner. They also suggest that cystic fibrosis infections should respond to increased levels of copper in airway fluid resulting from the administration of copper.

EXAMPLE 2

Enhancement of Magainin Antimicrobial Peptide Activity by Copper Ions

An experiment similar to that in Example 1 was carried out using magainin. As shown in Table 1 and FIG. 1, 0.01 to 0.1 mM CuS0$_4$ also enhanced the antimicrobial activity of this peptide.

EXAMPLE 3

Enhancement of Peptide #11 Antimicrobial Peptide Activity by Copper Ions

An experiment similar to that in Example 1 was carried out using peptide #11, a tryptophan-rich, 13 amino acid antimicrobial peptide having the amino acid sequence VRRFPWWWPFLRR (SEQ ID NO:3).

As shown in Table 1 and FIG. 1, 0.01 to 0.1 mM CuS0$_4$ also enhanced the antimicrobial activity of this peptide.

EXAMPLE 4

Enhancement of Tracheal Antimicrobial Peptide Activity by Copper Ions in the Presence of NaCl Smith ((1996) *Cell* 85:229) recently reported that cystic fibrosis airway epithelia fail to kill bacteria because of abnormal airway surface fluid, and speculated that a defensin-like molecule is involved.

Figure 2:
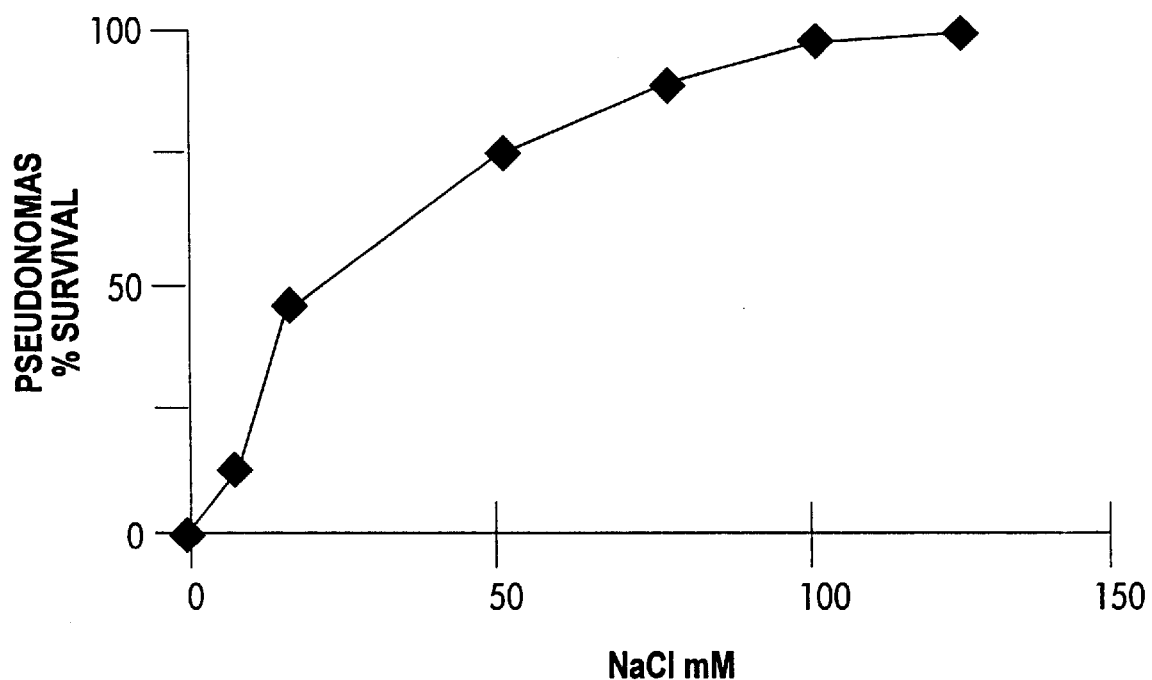
FIG. 2 shows the effects of 50 to 150 mM NaCl on the survival of Pseudomonas aeruginosa in the presence of Tracheal Antimicrobial Peptide (TAP; 10 ug/ml).

This experiment demonstrates that enhanced antimicrobial activity of TAP can be obtained by increasing the copper ion concentration, even in the presence of high concentrations of NaCl such as those found in cystic fibrosis airway surface fluid that are known to decrease the killing of *Pseudomonas aeruginosa* by TAP (the NaCl concentration on normal mucosal surfaces is approximately 75 mM; that in cystic fibrosis patients is approximately 116 mM). Note FIG. 2.

Bovine TAP of 38 amino acids was chemically synthesized by the method of Duclohier ((1989) *Biophys. J.* 5:1017–1021), and purified to a single peak by HPLC. Bactericidal assay was carried out by growing a wild-type Pseudomonas strain obtained from a cystic fibrosis patient in TSB until the OD$_{600}$ reached 0.2. Cells were then diluted in 50 µl 10 mM NaPO$_4$ buffer, pH 7.4, to 4×10$^5$ cells/ml. Ten µl/ml TAP, varying concentrations of NaCl, and 0.1 mM CuS0$_4$ were added, and the mixtures were incubated for 30 minutes at 37° C. Five µl samples were taken and plated on L-agar, and the plates were incubated at 37° C. overnight. Colonies were then counted.

The results are shown in Table 2.

TABLE 2

The Effect of Cu$^{++}$ and NaCl
On The Survival of *Pseudomonas aeruginosa*
In The Presence of TAP

| NaCl (mM) | TAP (µg/ml) | CU (mM) | % Survival | # Colonies |
|---|---|---|---|---|
| 0 | 0 | 0 | 100 | 1507 |
| 0 | 0 | 0 | 35 | 534 |

TABLE 2-continued

The Effect of $Cu^{++}$ and NaCl
On The Survival of *Pseudomonas aeruginosa*
In The Presence of TAP

| NaCl (mM) | TAP (μg/ml) | CU (mM) | % Survival | # Colonies |
|---|---|---|---|---|
| 15 | 0 | 0.1 | 39 | 580 |
| 25 | 0 | 0.1 | 34 | 513 |
| 50 | 0 | 0.1 | 46 | 696 |
| 75 | 0 | 0.1 | 53 | 796 |
| 15 | 10 | 0.1 | 15 | 233 |
| 25 | 10 | 0.1 | 6 | 89 |
| 50 | 10 | 0.1 | 16 | 242 |
| 75 | 10 | 0.1 | 24 | 363 |

These results demonstrate that the inhibitory effects of increasing NaCl concentrations on the killing of Pseudomonas by TAP (compare FIG. 2) can be overcome by providing copper, in this case at 0.1 mM. Thus, the combination of copper ions and TAP was more effective than TAP alone. We have demonstrated the same effect for $Mg^{++}$, which also inhibits TAP antimicrobial activity, as well.

Clinically, these results suggest that Pseudomonas infections should respond to elevation of the Cu level in airway surface fluid in cystic fibrosis patients.

Therapeutic and Other Applications

The results presented above demonstrate the effectiveness of supplemental metal ions in enhancing or maintaining the antimicrobial activity of antimicrobial peptides. Administration of metal ions to human or animal subjects being treated with antimicrobial peptides, lytic peptides, or peptide-derived antibiotics, either before, during, or after administration of the peptide, will either maintain the antimicrobial activity of the peptide under unfavorable conditions (e.g., in the presence of elevated NaCl levels), or substantially enhance the antimicrobial activity of the peptide, rendering it more therapeutically effective. Such enhancement can be in the range of from about 40% or more of the base level of activity of the peptide. Such metal ions can be administered to patients in non-toxic doses in the range of from about 10 μg to about 500 mg to achieve serum concentrations in the range of from about 0.001 mM to about 0.20 mM or more. Such metal ions can also be included in compositions comprising these peptides, for controlling the growth of disease-causing microorganisms within, on the internal and external surfaces of, and without the body, for example on surfaces requiring disinfection. In addition, such metal ions alone can be applied or administered to loci, or to subjects suffering from bacterial or fungal infection, where antimicrobial peptides, etc., are already present in order to enhance the activity of these peptides. For example, this has been discussed above in Examples 1 and 4 in connection with infections that occur in cystic fibrosis patients. Infections occurring in patients suffering from ketoacidosis can be similarly treated.

Peptides

Examples of peptides useful in the present invention include attacins, azurcidin, bactenecins, bombinin, cathelins, cecropin, ceratotoxins, cryptdins, defensins, levitides, magainins, mellitins, protegrins, ranalexins, sapecins, tachylesins, tachyplesins, thionins, and xenopsins.

Metal Ions

Metal ions useful in the present invention include, but are not limited to, ions of Cu, Al, Ag, Au, K, Mn, and B in their various valence states. For example, Cu can form salts as $Cu^+$, $Cu^{++}$, and $Cu^{+++}$.

Examples of copper salts useful in the present invention include copper sulfate (cupric sulfate), copper nitrate, copper phosphate, copper fluoride, copper gluconate, copper chelate, copper histadyl chelate, copper peptide chelate, copper EDTA, copper EGTA, cupric acetate, cupric borate, cupric bromide, cupric butyrate, cupric carbonate, cupric chlorate, cupric chloride, cupric chromate, cupric citrate, cupric formate, cupric glycinate, cupric hydroxide, cupric nitrate, cupric oleate, cupric oxalate, cupric oxide, cupric perchlorate, cupric phosphate, cupric salicylate, cupric selenate, cupric stearate, cupric sulfide, cupric tartrate, cuprous acetate, cuprous borate, cuprous bromide, cuprous butyrate, cuprous carbonate, cuprous chlorate, cuprous chloride, cuprous chromate, cuprous citrate, cuprous formate, cuprous glycinate, cuprous hydroxide, cuprous iodide, cuprous nitrate, cuprous oleate, cuprous oxalate, cuprous oxide, cuprous perchlorate, cuprous phosphate, cuprous salicylate, cuprous selenate, cuprous stearate, cuprous sulfide, and cuprous tartrate.

Examples of silver salts useful in the present invention include silver acetate, silver borate, silver bromide, silver butyrate, silver carbonate, silver chlorate, silver chloride, silver chromate, silver citrate, silver formate, silver glycinate, silver hydroxide, silver iodide, silver nitrate, silver oleate, silver oxalate, silver oxide, silver perchlorate, silver phosphate, silver salicylate, silver selenate, silver stearate, silver sulfide, and silver tartrate.

Examples of gold salts useful in the present invention include gold acetate, gold borate, gold bromide, gold butyrate, gold carbonate, gold chlorate, gold chloride, gold chromate, gold citrate, gold formate, gold glycinate, gold hydroxide, gold iodide, gold nitrate, gold oleate, gold oxalate, gold oxide, gold perchlorate, gold phosphate, gold salicylate, gold selenate, gold stearate, gold sulfide, and gold tartrate.

Examples of aluminum salts useful in the present invention include aluminum acetate, aluminum borate, aluminum bromide, aluminum butyrate, aluminum carbonate, aluminum chlorate, aluminum chloride, aluminum chromate, aluminum citrate, aluminum formate, aluminum glycinate, aluminum hydroxide, aluminum iodide, aluminum nitrate, aluminum oleate, aluminum oxalate, aluminum oxide, aluminum perchlorate, aluminum phosphate, aluminum salicylate, aluminum selenate, aluminum stearate, aluminum sulfide, and aluminum tartrate.

Examples of boron compounds and salts useful in the present invention include boric acid, sodium borate, and magnesium borate.

An example of a potassium salt useful in the present invention is potassium permanganate.

Examples of manganese salts useful in the present invention include manganese acetate, manganese borate, manganese bromide, manganese butyrate, manganese carbonate, manganese chlorate, manganese chloride, manganese chromate, manganese citrate, manganese dioxide, manganese formate, manganese glycinate, manganese hydroxide, manganese iodide, manganese nitrate, manganese oleate, manganese oxalate, manganese oxide, manganese perchlorate, manganese phosphate, manganese salicylate, manganese selenate, manganese stearate, manganese sulfide, and manganese tartrate.

The compositions disclosed herein can be used to control the growth of microorganisms susceptible to the antimicrobial activity of the peptides discussed herein. By "control the growth" is meant retarding or inhibiting the growth of, stopping the growth of, or killing, the microorganism. This results in a reduction in the adverse effects caused by the presence of the microorganism in any particular locus or milieu. These compositions can be formulated by conventional methods, and can contain formulation aids such as carriers, diluents, inert materials, surfactants, solvents, and other additives well known in the art. Pharmaceutically acceptable carriers are disclosed, for example, in The Pharmacopeia of the United States and the National Formulary. Using these formulations, mixtures of the present peptides with other antimicrobial substances, such as antibiotics, antifungals, etc., can also be prepared. Numerous conventional antibiotics and antifungals with which the present peptides and metal ions can be used are known in the art.

The methods of the present invention can be carried out in a variety of ways. The peptides, metal ions, and compositions discussed herein can be applied directly to loci where undesirable microorganisms are present, alone or in a mixture with other active ingredients, carriers, diluents, or other additives, including other antimicrobial agents, as is known in the art. Alternatively, these peptides and metal ions, alone or in combination, can be administered to human or animal subjects infected with such microorganisms to effect treatment.

Timing

The metal ion can be administered before, during, or after administration of the peptide. By "before" is meant a time period in the range of from about 6 hours to about 1 minute, more preferably from about 3 hours to about 15 minutes, most preferably from about 1 hour to about 30 minutes before administration of the peptide. By "after" is meant a time period in the range of from about 1 minute to about 3 hours, more preferably from about 15 minutes to about 2 hours, most preferably about 30 minutes to about 1 hour after administration of the peptide.

As ions of metals such as copper, silver, gold, aluminum, boron, etc., enhance the antimicrobial activity of the peptides discussed herein, the antimicrobial activity of these peptides in the loci where they are already present can be enhanced by the application or administration of such metal ions alone.

Doses

The compositions encompassed by the present invention include include those that can be applied to various surfaces external to the human body, such as countertops, medical instruments, and other surfaces requiring disinfection, and pharmaceutical compositions that can be applied or administered to the human body.

The concentrations and doses of peptides and metals useful in these various compositions are summarized below, listed in descending order, as preferred, more preferred, and most preferred ranges, respectively.

| Compositions | | |
|---|---|---|
| Peptide | Metal | Peptide + Metal |
| 0.001 µg/ml–500 mg/ml | 0.05 µg/ml–7.5 mg/ml | In each case, a combination of the preceding |
| 0.1 µg/ml–250 mg/ml | 0.1 µg/ml–5 mg/ml | |
| 1 µg/ml–100 mg/ml | 1 µg/ml–2.5 mg/ml | |

| Pharmaceutical Compositions | | |
|---|---|---|
| Peptide | Metal | Peptide + Metal |
| *Topical compositions* | | |
| 10 µg/ml–100 mg/ml | 1 µg/ml–5 g/ml | In each case, a combination of the preceding |
| 50 µg/ml–50 mg/ml | 10 µg/ml–2.5 g/ml | |
| 100 µg/ml–25 mg/ml | 100 µg/ml–1 g/ml | |
| *Internally administered compositions* | | |
| 100 µg–500 mg | 10 µg–500 mg | In each case, a combination of the preceding |
| 10 µg–250 mg | 50 µg–250 mg | |
| 1 µg–100 mg | 100 µg–100 mg | |

| Copper-Containing Compositions | | |
|---|---|---|
| Peptide | Metal | Peptide + Metal |
| *Compositions* | | |
| 0.001 µg/ml–1 g/ml | 0.05 µg/ml–5 g/ml | In each case, a combination of the preceding |
| 0.01 µg/ml–0.5 g/ml | 0.1 µg/ml–2.5 g/ml | |
| 0.1 µg/ml–0.25 g/ml | 1 µg/ml–1 g/ml | |
| *Pharmaceutical compositions* | | |
| *Tropical compositions* | | |
| 0.001 µg/ml–5 g/ml | 0.001 µg/ml–5 g/ml | In each case, a combination of the preceding |
| 0.01 µg/ml–2.5 g/ml | 0.01 µg/ml–2.5 g/ml | |
| 0.1 µg/ml–1 g/ml | 0.1 µg/ml–1 g/ml | |
| *Internally administered compositions* | | |
| 1 µg–5 g | 1 µg–300 mg | In each case, a combination of the preceding |
| 10 µg–2.5 g | 10 µg–150 mg | |
| 100 µg–1 g | 100 µg–75 mg | |

Metal ions can be used alone or in combination. Copper-containing pharmaceutical compositions of the present invention comprising metal ions for administration to human subjects should contain an amount of Cu ion sufficient to elevate the normal blood level thereof from approximately 0.01 mM to about 0.2 mM, although higher concentrations can be tolerated. 0.1 mM Cu can be applied topically to mucosal surfaces. On a percent weight basis of the total pharmaceutical composition, the peptide can comprise from about 0.1 to about 50% by weight, and the metal ion (or ions) can comprise from about 0.1 to about 50% by weight.

Formulations and Routes of Administration

Depending upon the specific application contemplated, the peptides and metal ions of the present invention can be formulated to be administered in a variety of ways known in the art. For example, they can be applied to surfaces or other loci in, on, or external to the body, or administered to the body, in the form of solutions, suspensions, parenteral preparations, sprays, aerosols, creams, lotions, ointments, gels, powders, tablets, capsules, suppositories, skin patches, drops (such as ear drops), etc. Parenteral preparations can include a vehicle such as specially distilled, pyrogen-free water, phosphate buffer, or normal saline. Ointments, creams, lotions, and sprays can include a carrier such as vegetable or mineral oil, white petrolatum, or a high molecular weight alcohol, i.e., an alcohol having a chain length greater than C12. Tablets or capsules can include diluents such as lactose, binders, lubricants such as stearic acid, and disintegrators such as corn starch. When administered to humans or animals, such formulations can be administered by any standard route of administration, including, but not limited to, orally, nasally, intramuscularly, intravenously, intraperitoneally, topically, intravaginally, into the urinary bladder, etc.

The compositions and methods of the present invention can be used to treat bacterial and fungal infections of, for example, mucosal surfaces, the nasal cavity, sinuses, the mouth, pharynx, trachea, lung, kidney, urinary bladder, gall bladder, vagina, urethra, prostate, gastrointestinal tract, and ear canal. All these surfaces produce antimicrobial peptides.

The present invention is therefore useful in preventative and therapeutic applications, treatment of infections, treatment and disinfection of various types of surfaces, etc.

The invention being thus described, it will be obvious that the same can be varied in many ways. Such variations are not to be regarded as a departure from the spirit and scope of the present invention, and all such modifications and equivalents as would be obvious to one skilled in the art are intended to be included within the scope of the following claims.

fluoride, copper gluconate, copper chelate, copper histadyl chelate, copper peptide chelate, copper EDTA, copper EGTA, cupric acetate, cupric borate, cupric bromide, cupric butyrate, cupric carbonate, cupric chlorate, cupric chloride, cupric chromate, cupric citrate, cupric formate, cupric glycinate, cupric hydroxide, cupric nitrate, cupric oleate, cupric oxalate, cupric oxide, cupric perchlorate, cupric phosphate, cupric salicylate, cupric selenate, cupric stearate, cupric sulfide, cupric tartrate, cuprous acetate, cuprous borate, cuprous bromide, cuprous butyrate, cuprous carbonate, cuprous chlorate, cuprous chloride, cuprous chromate, cuprous citrate, cuprous formate, cuprous glycinate, cuprous hydroxide, cuprous iodide, cuprous nitrate, cuprous oleate, cuprous oxalate, cuprous oxide, cuprous perchlorate, cuprous phosphate, cuprous salicylate, cuprous selenate, cuprous stearate, cuprous sulfide, and cuprous tartrate.

---

---

What is claimed is:

1. A composition, comprising:
   a peptide selected from the group consisting of tracheal antimicrobial peptide, peptide #11, attacins, azurcidin, bactenecins, bombinin, cathelins, ceratotoxins, cryptdins, levitides, protegrins, ranalexins, sapecins, tachylesins, tachyplesins, thionins, and xenopsins, and an ion of copper.

2. The composition of claim 1, wherein said peptide is present in an antimicrobial effective concentration, and said ion of copper is present in a concentration effective to enhance the antimicrobial activity of said peptide.

3. The composition of claim 1, wherein said ion of copper is selected from the group consisting of $Cu^+$, $Cu^{++}$, and $Cu^{+++}$.

4. The composition of claim 3, wherein said ion of copper is contained in a salt selected from the group consisting of cupric sulfate, copper nitrate, copper phosphate, copper 5. The composition of claim 2, wherein said antimicrobial effective concentration of said peptide is in the range of from about 0.001 µg/ml to about 500 mg/ml, and said effective concentration of said ion of copper is in the range of from about 0.05 µg/ml to about 7.5 mg/ml.

6. The composition of claim 1, further comprising a carrier or diluent.

7. A pharmaceutical composition, comprising:
   an antimicrobial effective amount of a peptide selected from the group consisting of tracheal antimicrobial peptide, peptide #11, attacins, azurcidin, bactenecins, bombinin, cathelins, ceratotoxins, cryptdins, levitides, protegrins, ranalexins, sapecins, tachylesins, tachyplesins, thionins, and xenopsins,
   an ion of copper in an amount effective to enhance the antimicrobial activity of said peptide, and
   a pharmaceutically acceptable carrier or diluent.

8. The pharmaceutical composition of claim 7, wherein said ion of copper is selected from the group consisting of $Cu^+$, $Cu^{++}$, and $Cu^{+++}$.

9. The pharmaceutical composition of claim 7, wherein said antimicrobial effective amount of said peptide is in the range of from about 100 µg to about 500 mg, and said effective amount of said ion of copper is in the range of from about 10 µg to about 500 mg.

10. The pharmaceutical composition of claim 7, in a form selected from the group consisting of a solution, a suspension, a parenteral preparation, a spray, an aerosol, a cream, a lotion, an ointment, a gel, a powder, a tablet, a capsule, a suppository, a skin patch, and a drop.

11. A method of enhancing the antimicrobial activity of a peptide, comprising administering or applying a peptide selected from the group consisting of tracheal antimicrobial peptide, peptide #11, attacins, azurcidin, bactenecins, bombinin, cathelins, ceratotoxins, cryptdins, levitides, protegrins, ranalexins, sapecins, tachylesins, tachyplesins, thionins, and xenopsins along with an ion of copper.

12. The method of claim 11, wherein said ion of copper is administered or applied prior to, simultaneously with, or subsequent to administering or applying said peptide.

13. A method of controlling the growth of a microorganism susceptible to the antimicrobial activity of a peptide selected from the group consisting of tracheal antimicrobial peptide, peptide #11, attacins, azurcidin, bactenecins, bombinin, cathelins, ceratotoxins, cryptdins, levitides, protegrins, ranalexins, sapecins, tachylesins, tachyplesins, thionins, and xenopsins, comprising providing to a locus where said microorganism is present said peptide and an ion of copper.

14. The method of claim 13, wherein said providing comprises applying or administering said ion of copper to said locus prior to, simultaneously with, or after applying or administering said peptide to said locus.

15. The method of claim 14, wherein said providing comprises applying or administering to said locus a composition comprising said peptide and said ion of copper.

16. A method for controlling the growth of a pathogenic microorganism susceptible to treatment with a peptide selected from the group consisting of tracheal antimicrobial peptide, peptide #11, attacins, azurcidin, bactenecins, bombinin, cathelins, ceratotoxins, cryptdins, levitides, protegrins, ranalexins, sapecins, tachylesins, tachyplesins, thionins, and xenopsins, comprising contacting said pathogenic microorganism with an antimicrobial effective amount of said peptide and an ion of copper, wherein said ion of copper is present at a concentration effective in maintaining or enhancing the antimicrobial activity of said peptide.

17. The method of claim 16, wherein said pathogenic microorganism is contacted with said ion of copper prior to, simultaneously with, or after said pathogenic microorganism is contacted with said peptide.

18. The method of claim 16, wherein said pathogenic microorganism is contacted with a composition comprising said peptide and said ion of copper.

19. A method of controlling the growth of a pathogenic microorganism, comprising contacting said pathogenic microorganism with a composition comprising an antimicrobial effective amount of a peptide selected from the group consisting of tracheal antimicrobial peptide, peptide #11, attacins, azurcidin, bactenecins, bombinin, cathelins, ceratotoxins, cryptdins, levitides, protegrins, ranalexins, sapecins, tachylesins, tachyplesins, thionins, and xenopsins, and an ion of copper, wherein said ion of copper is present at a concentration effective in maintaining or enhancing the antimicrobial activity of said peptide.

20. The method of claim 19, wherein said pathogenic microorganism is contacted directly with said composition, or wherein said composition is administered or applied to a human or animal subject infected with said pathogenic microorganism.

21. A method of treating a human or animal subject suffering from an infection caused by a microorganism susceptible to treatment with a peptide selected from the group consisting of tracheal antimicrobial peptide, peptide #11, attacins, azurcidin, bactenecins, bombinin, cathelins, ceratotoxins, cryptdins, levitides, protegrins, ranalexins, sapecins, tachylesins, tachyplesins, thionins, and xenopsins, comprising administering or applying to said human or animal subject a pharmaceutical composition, comprising:

an antimicrobial effective amount of said peptide, an ion of copper in an amount effective to maintain or enhance the antimicrobial activity of said peptide, and a pharmaceutically acceptable carrier or diluent.

22. A method of treating an airway infection due to a microorganism in a patient suffering from cystic fibrosis, comprising administering to said patient an amount of a metal ion effective to maintain or enhance the activity of tracheal antimicrobial peptide such that said tracheal antimicrobial peptide is effective in controlling the growth of said microorganism.

23. A method of treating an infection due to a microorganism in a patient suffering from ketoacidosis, comprising administering to said patient an amount of a metal ion effective to maintain or enhance the activity of a peptide having antimicrobial activity such that said peptide is effective in controlling the growth of said microorganism causing said infection, wherein said metal ion is selected from the group consisting of an ion of copper, an ion of silver, an ion of gold, an ion of boron, an ion of aluminum, and an ion of manganese.

24. The method of claim 22 or 23, wherein said metal ion is a copper ion.

25. The method of claim 24, wherein said copper ion is administered to said patient in an amount in the range of from about 1 µg to about 300 mg.

26. A kit, comprising:

a first container containing a peptide selected from the group consisting of tracheal antimicrobial peptide, peptide #11, attacins, azurcidin, bactenecins, bombinin, cathelins, ceratotoxins, cryptdins, levitides, protegrins, ranalexins, sapecins, tachylesins, tachyplesins, thionins, and xenopsins, and a second container containing an ion of copper.

27. A method of treating an infection due to a microorganism in a patient suffering from ketoacidosis, comprising administering to said patient an amount of an ion of copper effective to maintain or enhance the activity of a peptide having antimicrobial activity such that said peptide is effective in controlling the growth of said microorganism causing said infection, and wherein said administering is performed orally, nasally, topically, intravaginally, or into the urinary bladder.

* * * * *